United States Patent [19]
Lash

[11] Patent Number: 5,728,117
[45] Date of Patent: Mar. 17, 1998

[54] RETRACTABLE CAPSULORREHEXIS INSTUMENT

[76] Inventor: Roger S. Lash, 200 E. 87th St., Apt. 9J, New York, N.Y. 10128

[21] Appl. No.: 814,416

[22] Filed: Mar. 11, 1997

[51] Int. Cl.$^6$ ............................................. A61F 9/00
[52] U.S. Cl. ........................... 606/166; 606/107; 606/182
[58] Field of Search .................................. 606/107, 166, 606/172, 182

[56] References Cited

U.S. PATENT DOCUMENTS

| | | |
|---|---|---|
| 4,666,897 | 5/1987 | Smirmaul . |
| 4,785,810 | 11/1988 | Baccala et al. . |
| 4,844,065 | 7/1989 | Faulkner . |
| 4,959,070 | 9/1990 | McDonald ............................ 623/6 |
| 5,135,530 | 8/1992 | Lehmer ............................. 606/107 |
| 5,284,474 | 2/1994 | Adair ............................... 606/172 |

*Primary Examiner*—Gary Jackson
*Attorney, Agent, or Firm*—Cobrin Gittes & Samuel

[57] ABSTRACT

A capsulorrhexis instrument that is retractable within a tube and extendable into a position projecting out of the tube. The instrument comprises a flexible band having a razor sharp cutting edge which is fixed to a plunger and located within an inserter tube. While in its retracted position within the inserter tube, the flexible band assumes an elliptical or oblong shape. However, when the flexible band is in its extended position outside of the inserter tube such as inside the eye, it expands into a circular shape whose cutting edge is sufficiently sharp to cut lens capsular tissue in response to pressure being applied to the lens capsular tissue by the cutting edge. The dimension to which the flexible band expands to reach the circular shape upon becoming clear of the inserter tube is larger than a cross-section of the gap defined by the inserter tube through which the flexible band travels in its elliptical or oblong shape.

23 Claims, 4 Drawing Sheets

RETRACTABLE CAPSULORREHEXIS INSTUMENT

BACKGROUND OF THE INVENTION

1. Field of the Invention

The present invention relates to the field of apparatus for ophthalmic surgery. More particularly, the present invention relates to the field of apparatus for cataract surgery.

2. Description of the Related Art

With today's modem cataract surgery, it is routinely necessary to incise the anterior lens capsule of the crystalline lens of an eye to provide an opening on the anterior lens capsule so that the cataractous opaque lens can be removed. However, the anterior lens capsule of the eye is shielded by the corneal tissue. Therefore, before any cataract surgical apparatus can reach the anterior lens capsule of the eye, a passage wound has to be cut in the corneal tissue.

The following prior art patents are found to be related to the field of surgical apparatus used in cataract surgeries:

1. U.S. Pat. No. 4,959,070 issued to McDonald on Sep. 25, 1990 for "Intraocular Lens Implantation" (hereafter referred to as the "McDonald Patent").
2. U.S. Pat. No. 4,844,065 issued to Faulkner on Jul. 4, 1989 for "Intraocular Lens Inserting Tool and Methods" (hereafter referred to as the "/Faulkner Patent").
3. U.S. Pat. No. 4,785,810 issued to Baccala et al. on Nov. 22, 1988 for "Intraocular Lens Folding And Insertion Apparatus" (hereafter referred to as the "Baccala Patent").
4. U.S. Pat. No. 4,766,897 issued to Smirmaul on Aug. 30, 1988 for "Cataract Surgical Instrument" (hereafter referred to as the "Smirmaul Patent").
5. U.S. Pat. No. 5,135,530 issued to Lehmer on Aug. 4, 1992 for "Anterior Capsular Punch with Deformable cutting Member" (hereafter referred to as the "Lehmer Patent").

In the above five prior art patents, three of them, the Baccala Patent, the Faulkner Patent and the McDonald Patent, are not anterior lens capsule incising apparatus, but rather intraocular lens implanting apparatus. An anterior lens capsule incising apparatus is used in cataract surgery for cutting an incision on the anterior lens capsule of an eye, so that the natural lens of the eye can be removed and an artificial intraocular lens can be implanted therein. Alternatively, an intraocular lens implanting apparatus is used in the cataract surgery for inserting the artificial intraocular lens into the lens capsule of the eye, after the incision is cut on the anterior lens capsule of the eye and the natural crystalline lens of the eye is removed. The apparatuses envisioned by the Baccala Patent, the Faulkner Patent and the McDonald Patent are each more like a forceps apparatus because none of them contain cutting blades for performing the function of cutting the incision on the anterior lens capsule of the eye.

The Smirmaul Patent apparatus 10 is an anterior lens capsule incising apparatus. Its forward portion, including the circular lens holder 18, can be inserted through a passage wound cut on the corneoscleral tissue of an eye, and disposed above the anterior lens capsule of the eye, so that its rotatable cutting blade 20 can cut a circular incision on the anterior lens capsule. The Smirmaul Patent incising apparatus 10 requires a wide passage wound cut on the corneoscleral tissue. The diameter of the rotatable circular cutting blade 20 of the Smirmaul Patent incising apparatus 10 is about six millimeters (6 mm) (Column 3, line 23), which is the necessary size for cutting an adequate incision on the anterior lens capsule for further surgeries. Therefore the overall diameter of the circular blade holder is at least above seven millimeters (7 mm). This requires that the width of the passage wound cut on the corneoscleral tissue to be not less than seven millimeters (7 mm), which is wide by eye surgery standards. It is desirable to have the width of the passage wound cut on the corneoscleral tissue as narrow as possible, since a wider wound requires more surgical closing procedures and increases the period of convalescence.

The Lehmer Patent discloses an annular capsular punch with a deformable cutting member. A cutting member 130 is elliptical when inserted through an incision 16 on the corneoscleral tissue of the eye. Once the cutting instrument 130 is in the anterior chamber of the eye, it is allowed to expand a circular shape and then pressed against the anterior lens capsule of the eye.

According to the Lehmer patent, the circular shape would have a circular cutting blade having a diameter of not less than five millimeters (5 mm). Additionally, the preferable anterior lens capsule incising apparatus should be able to pass through a narrow corneoscleral tissue wound having a width of not more than four millimeters (4 mm).

This deformable circular cutting ting is provided between the two forward portions of two elongated arms. The two elongated arms crisscross each other and are hinged together at the crisscross joint. The rearward portion of the two arms are spring biased to keep the forward portion of the two arms spaced apart, such that the deformable circular cutting ring is in its original circular shape. When the rearward portions of the two arms are squeezed toward each other, the forward portions of the two arms will move toward each other to compress the deformable circular cutting ring into a narrow elliptical shape.

The overall width of the narrow elliptical shaped deformable circular cutting ring and the forward portions of the two elongated arms become less than four millimeters (4 mm), so that the narrow elliptical shaped deformed cutting ting and the forward portions of the two elongated arms can be inserted into the anterior chamber of the eye through a narrow corneoscleral tissue wound of about four millimeters (4 mm) in width. The crisscross joint of the two elongated arms is located at or adjacent to the corneoscleral tissue wound.

Once inside the anterior chamber of the eye, the rearward portions of the two arms are released, so that the forward portions of the two arms can move away from each other to allow the deformable circular cutting ring return to its original circular shape. Then the full size circular cutting ring is pressed onto the anterior lens capsule to cut an adequate sized circular incision, so the natural crystalline lens of the eye can be removed, and an artificial intraocular lens can be implanted therein. The deformable circular cutting ring is taken out of the anterior chamber through the narrow wound on the corneoscleral tissue by again compressing it into a narrow elliptical shape.

Also, a locking mechanism is to be provided to the anterior lens capsule incising apparatus for preventing the deformable cutting ring from rotating about its axis, so that the cataract surgeon can control the exact orientation of the deformable cutting ring and the cutting edge of the deformable cutting ring is evenly applied on the anterior lens capsule.

It is desirable to provide a reliable tool for performing capsulorrhexis through a small incision cataract without the unpredictability, inconsistency and unreliability of capsulorrhexis performed with a cystatome and/or capsulorrhexis forceps and which operates in a manner different from conventional teachings of tools for carrying out a capsulorrhexis.

SUMMARY OF THE INVENTION

One aspect of the present invention resides in a capsulorrhexis instrument that is retractable within a tube and extendable into a position projecting out of the tube. The instrument comprises a flexible band having a razor sharp cutting edge which is fixed to a plunger and located within an inserter tube. While in its retracted position within the inserter tube, the flexible band assumes an elliptical or oblong shape. However, when the flexible band is in its extended position outside of the inserter tube such as inside the eye, it deforms into a circular shape whose cutting edge is sufficiently sharp to cut corneal tissue in response to pressure being applied to the corneal tissue by the cutting edge. The dimension to which the flexible band expands to reach the circular shape upon becoming clear of the inserter tube is larger than a cross-section of the gap defined by the inserter tube through which the flexible band travels in its elliptical or oblong shape.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 2:
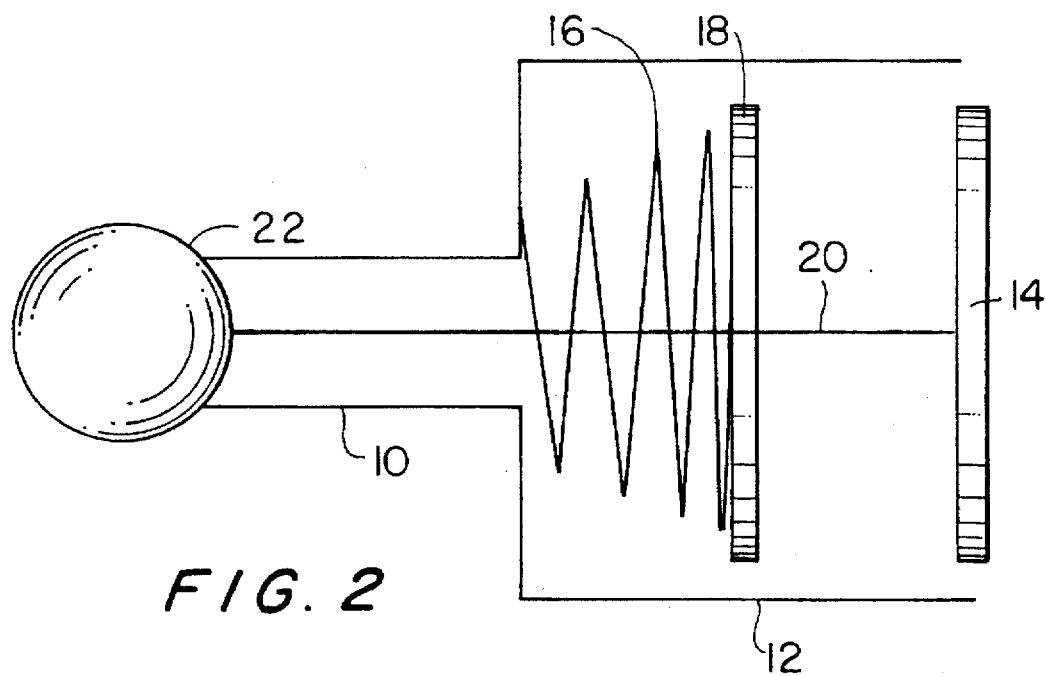
FIG. 2 is a schematic representation of the instrument of FIG. 1 except with its band in an extended position.
Figure 1:
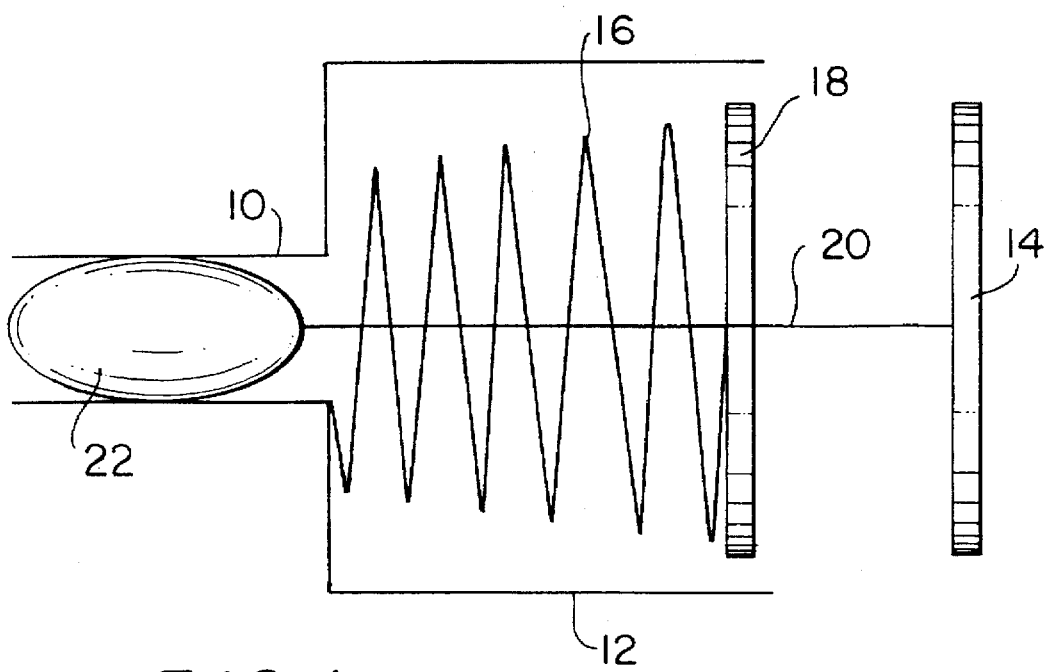
FIG. 1 is a schematic representation of a capsulorrhexis instrument in accordance with the invention with its band in a retracted position.

FIGS. 1 and 2 show an introducer tube 10, a plunger housing 12, and plunger 14, and a spring 16 that biases the head disc 18 within the plunger housing 12. A stem 20 extends from the head disc 18 and a flexible band 22 is connected to the free end of the stem 20.

The operation of the plunger within the plunger housing is in accord with conventional teachings in other arts. The flexible band, however, changes from an elliptical or oblong configuration when residing within the introducer tube in the fully retracted position of FIG. 1 to a circular configuration while emerging free of the introducer tube to reach the fully extended position of FIG. 2.

The flexible band 22 is normally in the circular condition while in an uncompressed state, but resiliently flexes into the elliptical or oblong condition when squeezed into the introducer tube that has a smaller cross-section. The flexible band may be constructed of metal or any other material with at least one razor sharp edge 24 as identified in FIG. 6. Preferably, the other edge is smooth.

The plunger may be plastic or metal construction. The plunger housing 12 serves as a handle for a surgeon to hold onto. The inserter tube may have an inner diameter of 1½–3 mm and the flexible band in its circular configuration may have a 4–8 mm inner diameter.

Figure 3:
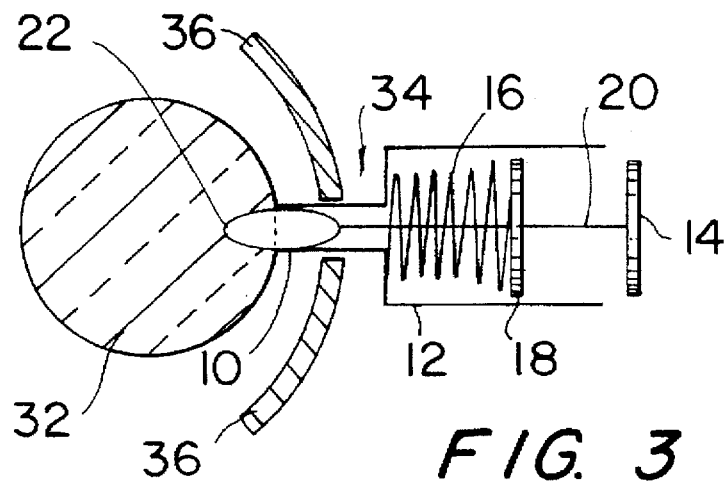
FIGS. 3–5 are progressive schematic representations of the capsulorrhexis instrument of FIGS. 1–2 in use showing the flexible band in, respectively, the retracted position, the extended position and the retracted position after cutting.
Figure 4:
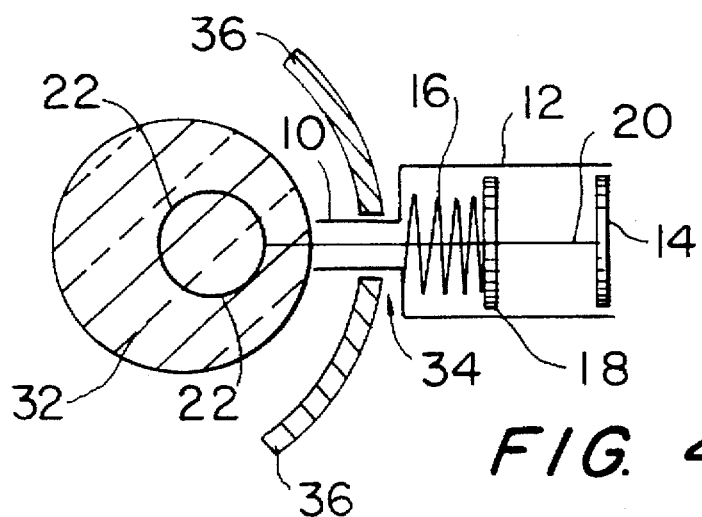
Figure 5:
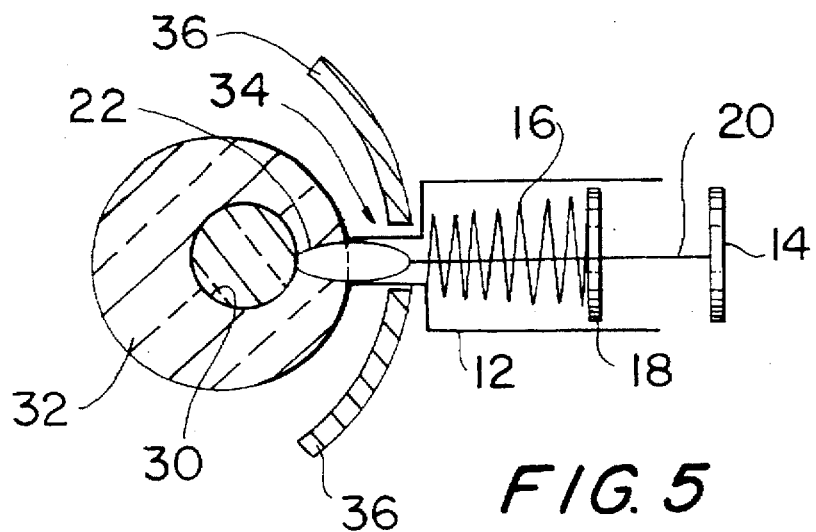

Before an incision 30 can be cut on the anterior lens capsule 32 of an eye for removing the natural crystalline lens of the eye and implanting an artificial intraocular lens therein, a small wound 34 must be cut on the corneoscleral tissue 36 of the eye to gain access to the anterior chamber of the eye, which anterior chamber is shown in FIGS. 3 through 5 by the space between the anterior lens capsule 32 and the corneoscleral tissue 36. It is preferable to have a small and narrow corneoscleral wound 34, preferably not more than three millimeters (3 mm) in width. However, the size of the anterior capsular incision 30 should be no less than five millimeters (5 mm). The present invention solves this problem by utilizing the deformable flexible band 22 with a sharp edge 24.

In addition, a viscoelastic material, such as Healon™, Amvisc™, Viscoat™ or Vitrax™, must be injected to fully expand the anterior lens chamber prior to use of the capsulorrhexis instrument, as is done conventionally. Such chamber expansion is needed before the surgery can be performed to avoid tissue damage as the flexible band is inserted into position for cutting.

To insert the flexible band 22 into the anterior chamber of the eye, the flexible band 22 is initially retracted within the introducer tube 10 as the distal end of the introducer tube is inserted through the narrow corneoscleral wound 34. Thereafter, the plunger 14 is forced against spring bias to force the flexible band 22 out of the introducer tube 10 and into the anterior chamber of the eye but clear of the narrow corneoscleral wound 34. Once so free, the flexible band 22 resiliently flexes from the elliptical shape to return to its original circular shape.

As the deformable flexible band 22, now circular in shape, is accurately located above the anterior lens capsule 32 of the eye, a force is applied on the flexible band 22 directed perpendicular to the insertion direction via the stem 20 to cut the incision 30 to have an adequate size, typically about five millimeters (5 mm) in diameter. This cutting process is done while keeping the distal end of the introducer tube 10 at or adjacent the narrow corneoscleral wound 34, so that further swings of the introducer tube will not require a wider wound. To effect the cutting, the surgeon presses on the anterior lens capsule, thereby providing the force through anterior lens capsule that is necessary for the sharp edge to cut.

Figure 6:
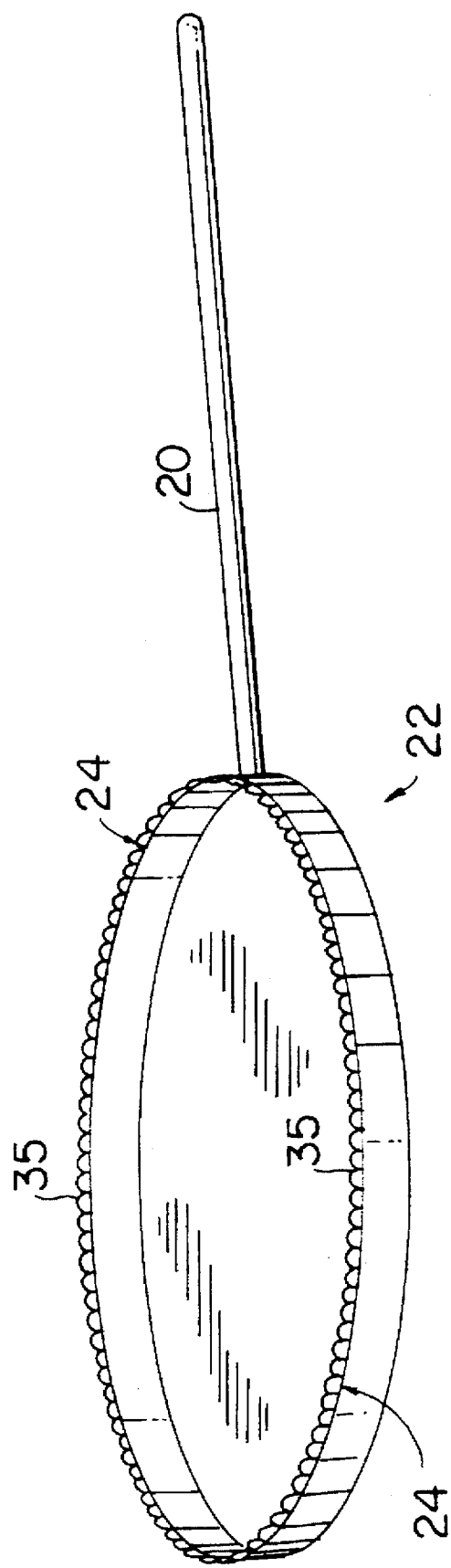
FIG. 6 is a perspective view of the flexible band with dye.

If desired, a non-toxic dye 35 such as fluorescein may be applied to the sharp edge 24 to serve as a marker for the surgeon as to where the cut was made (see FIG. 6). Thus, as the sharp edge comes into contact with tissue to effect cutting, the dye comes off and onto the tissue, thereby leaving a visual imprint along the boundary of incision 30 (see FIG. 5).

After the incision 30 is made, the plunger 14 is released (e.g., via spring bias) into the introducer tube 10 so as to form the flexible band 22 by compressing the flexible band 22 into the narrow elliptical shape. Once the plunger is fully retracted, the introducer tube 10 can be withdrawn from the anterior chamber through the narrow corneoscleral wound 34. The flexible band 22 and introducer tube 10 are intended to be disposable as a single use item.

An advantage of the present invention lies in that the introducer tube may have a width of as small as 1½ mm, easily fitting within incisions as small as 2.5 mm. In the past, incisions were typically in the order of 4 mm, which gave extra room to accommodate capsulorrhexis instruments of larger dimensions. However, with incisions as small as 2.5. mm, the need for smaller dimensioned capsulorrhexis instruments is apparent, particular when one considers that incisions in the future will be still smaller in size.

The configuration of the capsulorrhexis instrument may be curved to accommodate performing cataract surgery from above the forehead of the patient where it may be difficult to circumvent the brow of the patient. If the cataract surgery is performed from the side of the eye of the patient, then no such curvature is needed.

There are various embodiments to aid the surgeon in knowing when the flexible band has reached its fully extended state or has been withdrawn into its fully retracted state. In all cases, full retraction would be from visual observation.

One embodiment employs a locking mechanism that locks the flexible band in the extended position as the plunger is pushed to an intermediate position (closer to the fully extended position) such as 95% of the way and that unlocks the flexible band from that extended position as the plunger is pushed the rest of the way to the fully extended position, such as the remaining 5%. This simulates the locking mechanism of a ballpoint pen by allowing the flexible band to alternate between the fully extended and fully retracted states. Starting from the fully retracted position, the plunger is pushed as far as possible until further movement is blocked at a blocking position by the mechanism and is then released. The release allows the spring bias to force the plunger into the 95% position where the flexible band is fully expanded, thereby positioning the band for cutting. When done cutting, the plunger is again pushed as far as possible until blocked, but this time release causes the spring bias to force the plunger all the way back to the fully retracted position. Such continues in an alternating manner as much as desired as in actuation of a ballpoint pen.

Another embodiment dispenses with the locking mechanism, but the plunger is blocked upon reaching full extension and this blocking is felt as a noticeable increase in resistance to pushing of the plunger. In this manner, the surgeon comes to realize that the flexible band has reached its fully expanded state. Thus, the procedure followed by the surgeon is making an incision in the eye, placing the introducer tube at or into the incision, pushing the plunger until the flexible band has emerged from the introducer tube into its fully expanded state, feeling the resistance to further movement in the direction of pushing, engaging the anterior lens capsule and pressing the same to cut tissue with the sharp edge of the flexible band, releasing the plunger to retract the flexible band back into the introducer tube, and removing the introducer tube from the eye.

Figure 7:
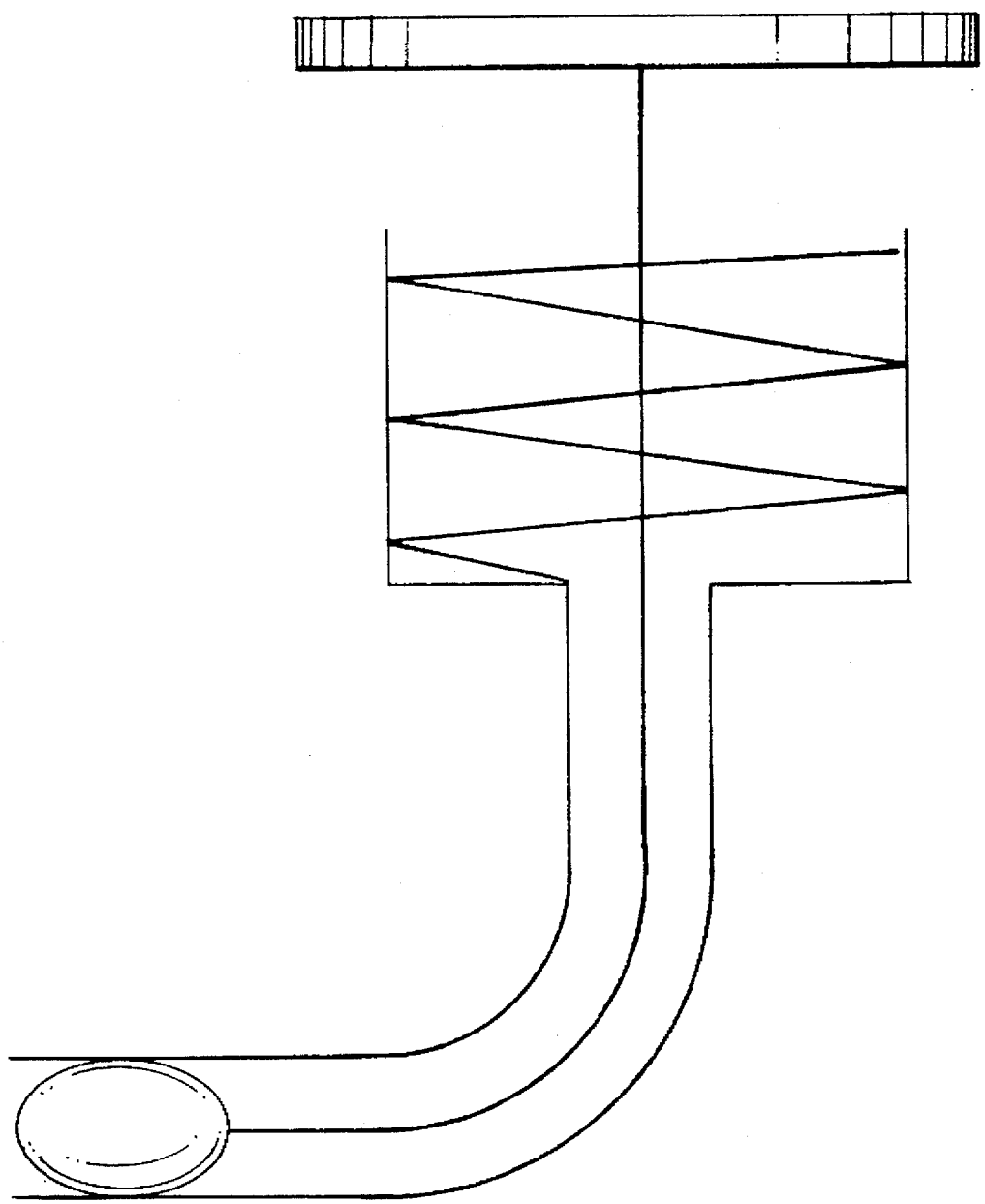
FIG. 7 is a schematic elevational view of a further embodiment.

Still another embodiment locks or clicks when the flexible band clears the edge of the introducer tube and a further embodiment that locks in after the plunger stem extends several millimeters into the eye to space the flexible band from the introducer tube to allow for more maneuvering of the expanded band if the surgeon wished to place the cut in a more posterior or lateral or medial position. However, for most surgeries where the incision is 2.5 mm, allowing the locking or clicking to arise as the flexible band expands at the edge of the introducer tube provides plenty of maneuverability without opening the incision further provided the introducer tube has a width of at most 2 mm.

Where the eye is particularly deep-set, however, additional maneuverability may be needed so it would be more advantageous to keep the inserter tube outside the incision and pen the band further inside the eye by a few millimeters with a longer and curved plunger stem such a curved stem as shown in FIG. 7 allows better access to the eye where the surgery is to be conducted from above the forehead as opposed to the side. To prevent the possibility of the expanded flexible band springing back inadvertently into the introducer tube while the introducer tube is outside the incision, a spring release mechanism would need to be actuated by the surgeon to release the spring.

While the preferred embodiment employs a spring bias to retract the flexible band into the inserter tube, the spring bias could instead be opposite to push the flexible band out of the inserter tube. Also, the spring could be dispensed with altogether, but such would require greater dexterity on the part of the surgeon to steady the inserter tube in its relative position to the eye as the flexible band is either pulled into the inserter tube or forced out. The inserter tube may be of uniform dimension along its full length, such as having an inner diameter of about 2 mm. The inserter tube need not be narrower at its distal end through which the flexible band emerges or retracts. If a spring is to be used, however, an inwardly directed projection about the inner periphery at an intermediate location of the inserter tube is needed to provide the spring with a surface against which it may compress. Of course, a wider proximal end is more advantageous for grasping purposes.

While the foregoing description and drawings represent the preferred embodiments of the present invention, it will be understood that various changes and modifications may be made without departing from the spirit and scope of the present invention.

What is claimed is:

1. A capsulorrhexis instrument, comprising a plunger housing;

a plunger within said housing movable between fully retracted and fully extended positions, said plunger housing blocking further movement of said plunger beyond said fully extended position; and a flexible band movable with said plunger so as to be within said plunger housing as said plunger reaches said retracted position and to be clear of said plunger housing as said plunger reaches said fully extended position, said flexible band compressing in response to entering into said plunger housing and expanding in response to emerging from said plunger housing, said plunger housing defining a chamber through which said flexible band moves while traveling between said fully retracted position and fully extended position, said chamber defining a gap with a cross-section smaller than a width to which the flexible band expands into upon clearing said plunger housing, said flexible band having a cutting edge that is sharp sufficient to cut lens capsular tissue in response to pressure being applied to force said cutting edge against the lens capsular tissue.

2. An instrument as in claim 1, wherein said flexible band has an elliptical configuration while said plunger is in said fully retracted position and a circular configuration while said plunger is in said fully extended position.

3. An instrument as claim 1, wherein said flexible band resiliently compresses into a compressed condition as said plunger enters said retracted position and resiliently expands into an uncompressed condition as said plunger enters said extended position.

4. An instrument as in claim 1, further comprising a spring within said housing that biases said plunger into said retracted position.

5. An instrument as in claim 1, further comprising a spring within said housing that biases said plunger into said extended position.

6. An instrument as in claim 1, said plunger includes a head and a stem extending from said head, said flexible band being connected to said stem.

7. An instrument as in claim 1, further comprising a dye on said cutting edge that comes off in response to pressing against the lens capsular tissue.

8. An instrument as in claim 1, further comprising a mechanism attached to said plunger housing to force said plunger under spring bias to reach in alternating manner said fully retracted position and an intermediate position, said intermediate position being closer to said fully extended position than to said fully retracted position, said mechanism releasing said plunger from said intermediate position to reach said fully retracted position only after said plunger leaves said fully extended position.

9. An instrument as in claim 8, wherein said flexible band just clears said plunger housing to enter into a fully expanded state in response to said plunger reaching said intermediate position.

10. An instrument as in claim 8, wherein said flexible band is spaced from said plunger housing at said intermediate position.

11. An instrument as in claim 1, further comprising an arm having a curvature attached to said plunger housing.

12. An instrument as in claim 8, wherein said plunger housing has a curvature.

13. An instrument as in claim 1, further comprising a stem attached to said plunger, said stem having a curvature.

14. An instrument as in claim 1, wherein said plunger includes a head with threads, said plunger housing having an inner surface that is threaded to mate with said threads, said plunger further including a stem extending from said head, said flexible band being connected to said stem.

15. A method of operating a capsulorrhexis instrument, comprising the steps of:

moving a plunger through a chamber of a housing from a fully retracted position to a fully extended position;

blocking further movement in the same direction traveled by the plunger in reaching the fully extended position as the plunger reaches the fully extended position; and moving a flexible band in unison with the plunger such that the flexible band is within the chamber of the housing as the plunger reaches the retracted position and clear of the housing as the plunger reaches the extended position, the flexible band compressing in response to entering into said plunger housing and expanding in response to emerging from said plunger housing, said chamber defining a gap whose cross-section is smaller than a width to which the flexible band expands after emerging from said plunger housing, the flexible band having a cutting edge that is sharp sufficient to cut lens capsular tissue in response to pressure being applied to force said cutting edge against the lens capsular tissue.

16. A method as in claim 15, wherein said flexible band has an elliptical configuration while said plunger is in said fully retracted position and a circular configuration while said plunger is in said fully expanded position.

17. A method as in claim 15, wherein said flexible band resiliently compresses into a compressed condition as said plunger enters said fully retracted position and resiliently expands into an uncompressed condition as said plunger enters into said fully extended position.

18. A method as in claim 15, further comprising spring biasing the plunger into the fully retracted position.

19. A method as in claim 15, wherein the step of moving the plunger includes forcing the plunger in a direction against a spring bias, the spring bias biasing the plunger into the fully retracted position.

20. A method as in claim 15, wherein the step of moving the plunger includes rotating the plunger relative to the housing to advance the plunger into the fully extended position.

21. A method as in claim 15, further comprising the steps of applying a dye to the cutting edge that comes off onto the lens capsular tissue in response to application of the pressure.

22. A method as in claim 15, further comprising the steps of retaining the plunger at an intermediate position that is closer to the fully extended position than to the fully retracted position and releasing the plunger from the intermediate position to reach the fully retracted position only after the plunger leaves the fully extended position.

23. A method as in claim 22, further comprising the step of steadying the introducer tube from a position above the forehead of a patient and around a brown of the patient.

* * * * *